United States Patent [19]
Chan

[11] Patent Number: 6,162,237
[45] Date of Patent: Dec. 19, 2000

[54] TEMPORARY INTRAVASCULAR STENT FOR USE IN RETROHEPATIC IVC OR HEPATIC VEIN INJURY

[76] Inventor: Winston Kam Yew Chan, 4666 Charing Cross Rd., Bloomfield Hills, Mich. 48304

[21] Appl. No.: 09/294,286

[22] Filed: Apr. 19, 1999

[51] Int. Cl.⁷ .................................................. A61M 29/00
[52] U.S. Cl. ............................................................. 606/198
[58] Field of Search ................................ 604/95, 96, 97; 606/191, 198, 200; 623/1.11, 1.13

[56] References Cited

U.S. PATENT DOCUMENTS

| | | |
|---|---|---|
| Re. 35,849 | 7/1998 | Soehendra . |
| 3,721,233 | 3/1973 | Montgomery et al. . |
| 4,212,304 | 7/1980 | Finney . |
| 4,580,568 | 4/1986 | Gianturco . |
| 4,639,252 | 1/1987 | Kelly et al. . |
| 4,713,049 | 12/1987 | Carter . |
| 4,790,809 | 12/1988 | Kuntz . |
| 4,800,882 | 1/1989 | Gianturco . |
| 4,820,298 | 4/1989 | Leveen et al. . |
| 4,907,336 | 3/1990 | Gianturco . |
| 4,950,226 | 8/1990 | Barron . |
| 4,955,859 | 9/1990 | Zilber . |
| 4,957,479 | 9/1990 | Roemer . |
| 4,990,155 | 2/1991 | Wilkoff . |
| 4,998,539 | 3/1991 | Delsanti .................................. 606/198 |
| 5,035,706 | 7/1991 | Gianturco . |
| 5,064,434 | 11/1991 | Haber ...................................... 606/198 |
| 5,129,910 | 7/1992 | Phan et al. . |
| 5,151,105 | 9/1992 | Kwan-Gett . |
| 5,160,341 | 11/1992 | Brenneman et al. . |
| 5,176,626 | 1/1993 | Soehendra . |
| 5,190,058 | 3/1993 | Jones et al. . |
| 5,222,969 | 6/1993 | Gillis . |
| 5,222,971 | 6/1993 | Willard et al. . |
| 5,261,878 | 11/1993 | Galindo . |
| 5,263,963 | 11/1993 | Garrison et al. ......................... 606/198 |
| 5,282,784 | 2/1994 | Willard . |

(List continued on next page.)

OTHER PUBLICATIONS

Factors Related to Mortality in Inferior Vena Cava Injuries—A 5 Year Experience; Raul Coimbra; Int. Surg. 1994; pp. 138–141.

Injuries of the Inferior Vena Cava; Mark T. Stewart; The American Surgeon;1985; pp. 9–13.

Injuries of the Inferior Vena Cava; Jon M. Burch; The American Journal of Surgery, vol. 156, Dec. 1988; pp. 548–552.

A New Technique for Exposure of Injuries at the Confluence of the Retrohepatic Veins and the Retrohepatic Vena Cava; The Journal of Trauma; vol. 30, No. 3; pp. 328–331.

Massive Liver Trauma Involving the Suprarenal Vena Cava; The American Journal of Surgery; pp. 960–963.

Atrial Caval Shunting in Blunt Hepatic Vascular Injury; Peter F. Rovito; pp. 318–321.

(List continued on next page.)

*Primary Examiner*—David J. Isabella
*Attorney, Agent, or Firm*—Brinks Hofer Gilson & Lione

[57] ABSTRACT

A temporary stent for use in retrohepatic IVC or hepatic vein injury which is capable of expanding to the appropriate size of a blood vessel without reducing preload. According to the preferred first embodiment, the stent includes an outer sheath made of a very thin, expandable and impermeable material. An internal skeleton is comprised of a plurality of axial support members. At one end the axial support members terminate collectively on an inner guide wire. At the other end the axial support members terminate collectively on an outer guide wire. In a second embodiment, a rotatable gear arrangement is provided with two shafts for selectively playing out and reeling in an expandable sheath. According to this embodiment, the stent sheath is movable between a rolled position and an unrolled position and is unrolled once delivered to the desired site. Optionally, the stent of the present invention may be fitted with probes so that the stent might demonstrate ultrasonic assessment capabilities to allow exacting implantation.

21 Claims, 5 Drawing Sheets

U.S. PATENT DOCUMENTS

| | | |
|---|---|---|
| 5,282,824 | 2/1994 | Gianturco . |
| 5,287,861 | 2/1994 | Wilk . |
| 5,314,444 | 5/1994 | Gianturco . |
| 5,322,501 | 6/1994 | Mahmud-Durrani . |
| 5,334,208 | 8/1994 | Soehendra et al. . |
| 5,344,444 | 9/1994 | Glastra . |
| 5,350,398 | 9/1994 | Pavcnik et al. . |
| 5,356,423 | 10/1994 | Tihon et al. . |
| 5,368,566 | 11/1994 | Crocker . |
| 5,411,549 | 5/1995 | Peters . |
| 5,421,955 | 6/1995 | Lau et al. . |
| 5,443,477 | 8/1995 | Marin et al. ............................ 606/198 |
| 5,443,500 | 8/1995 | Sigwart . |
| 5,449,372 | 9/1995 | Schmaltz et al. . |
| 5,456,667 | 10/1995 | Ham et al. .............................. 606/198 |
| 5,470,307 | 11/1995 | Lindall . |
| 5,474,563 | 12/1995 | Myler et al. . |
| 5,484,449 | 1/1996 | Amundson et al. . |
| 5,498,240 | 3/1996 | Bagaoisan et al. . |
| 5,522,882 | 6/1996 | Gaterud et al. . |
| 5,545,135 | 8/1996 | Iacob et al. . |
| 5,549,122 | 8/1996 | Detweilwer . |
| 5,556,414 | 9/1996 | Turi . |
| 5,558,081 | 9/1996 | Lipkin . |
| 5,571,086 | 11/1996 | Kaplan et al. . |
| 5,612,885 | 3/1997 | Love . |
| 5,624,450 | 4/1997 | Glastra . |
| 5,628,754 | 5/1997 | Shevlin et al. . |
| 5,630,830 | 5/1997 | Verbeek . |
| 5,634,941 | 6/1997 | Winston et al. . |
| 5,643,277 | 7/1997 | Soehendra et al. . |
| 5,643,309 | 7/1997 | Myler et al. . |
| 5,643,314 | 7/1997 | Carpenter et al. . |
| 5,647,857 | 7/1997 | Anderson et al. . |
| 5,649,906 | 7/1997 | Gory et al. . |
| 5,653,744 | 8/1997 | Khouri . |
| 5,676,685 | 10/1997 | Razavi . |
| 5,690,643 | 11/1997 | Wijay . |
| 5,690,644 | 11/1997 | Yurek et al. . |
| 5,693,066 | 12/1997 | Rupp et al. . |
| 5,716,410 | 2/1998 | Wang et al. . |
| 5,722,979 | 3/1998 | Kusleika . |
| 5,730,698 | 3/1998 | Fischell et al. . |
| 5,733,302 | 3/1998 | Myler et al. . |
| 5,733,884 | 3/1998 | Barbul et al. . |
| 5,735,869 | 4/1998 | Fernandez-Aceytuno . |
| 5,743,874 | 4/1998 | Fischell et al. . |
| 5,749,848 | 5/1998 | Jang et al. . |
| 5,749,883 | 5/1998 | Halpern .................................. 606/198 |
| 5,749,914 | 5/1998 | Janssen . |
| 5,755,770 | 5/1998 | Ravenscroft . |
| 5,756,464 | 5/1998 | Scannon et al. . |
| 5,766,192 | 6/1998 | Zacca . |
| 5,766,237 | 6/1998 | Cragg . |
| 5,767,160 | 6/1998 | Kaesemeyer . |
| 5,776,140 | 7/1998 | Cottone . |
| 5,782,903 | 7/1998 | Wiktor . |
| 5,785,715 | 7/1998 | Schatz . |
| 5,795,319 | 8/1998 | Ali . |
| 5,800,522 | 9/1998 | Campbell et al. . |
| 5,807,327 | 9/1998 | Green et al. . |
| 5,833,651 | 11/1998 | Donovan et al. . |
| 6,013,019 | 1/2000 | Fischell et al. ........................ 606/198 |

OTHER PUBLICATIONS

The Ongoing Challenge f Retroperitoneal Vascular Injuries; Raul Coimbra; Ther American Journal of Surgery; vol. 172; Nov. 1996; pp. 541–545.

Management of Retrohepatic Venous Injuries with Atrial Caval Shunts; Aorn Journal; pp. 376–382.

The Atriocaval Shunt Facts and Fiction; Jon Burch; Ann. Surg.; pp. 555–568.

Succesful Atrial Caval Shunting in the Management of Retrohepatic Venous Injuries; Sandra L. Beal; The American Journal of Surgery; vol. 158; Nov. 1989; pp. 409–413.

Inferior Vena Cava Injuries–The Challenge Continues; Robert G. Wiencek, Jr.; The American Surgeon; Jul. 1998; pp. 423–428.

Vascular Ultrasound Today; Lesson 5; vol. 3; May 1998.

Surgical Management of Injuries to the Vena Cava: Changing Patterns of Injury and Newer Techniques of Repair; Donald L. Bricker; The Journal of Trauma; vol. 11, No. 9; pp. 725–735.

Contemporary Management Strategy for Major Inferior Vena Caval Injuries; Stanley R. Klein; The Journal of Trauma; vol. 37, No. 1; pp. 35–42.

Vascular Exclusion in Surgery of the Liver—Experimental Basis, Technic and Clinic Results; P. Testas; The American Journal of Surgery; pp. 692–696.

Traumatic Inferior Vena Caval Injuries; Ari K. Leppaniemi; Scand J Thor Cadiovasc Surg 28; 1994; pp. 103–108.

Trauma, Second Edition; Ernest E. Moore; pp. 441–463.

Temporary Internal Vascular Shunt for Retrohepatic Vena Cava Injury; Robert S. Brown; The Journal of Trauma; pp. 736–737.

Hepatic Venous Injury; A case Report of Atriocaval Shunt by a Centrifugal Pump; Satoshi Taga; Hepato–Gastroenterology 44 vol. 67, No. 4; 1997.

Vena Cava Catheter for Assanguineous Liver Resection; Surgery; vol. 67, No. 4; Apr. 1970; pp. 694–696.

Retrohepatic Vena Cava Balloon Shunt Introduced Via the Sapheno–Femoral Junction; David B. Pilcher; vol. 17, No. 11; pp. 837–841.

Management of Penetrating Juxtahepatic Inferior Vena Cava Injuries Under Total Vascular Occlusion Satish C. Khaneja; Journal of the American College of Surgeons; May 1997; vol. 184; pages.

Insertion of a Retrohepatic Vena Cava Balloon Shunt Through the Saphenofemoral Junction; Oliver J. McAnena; The American Journal of Surgery; vol. 158; Nov. 1989; pp. 463–466.

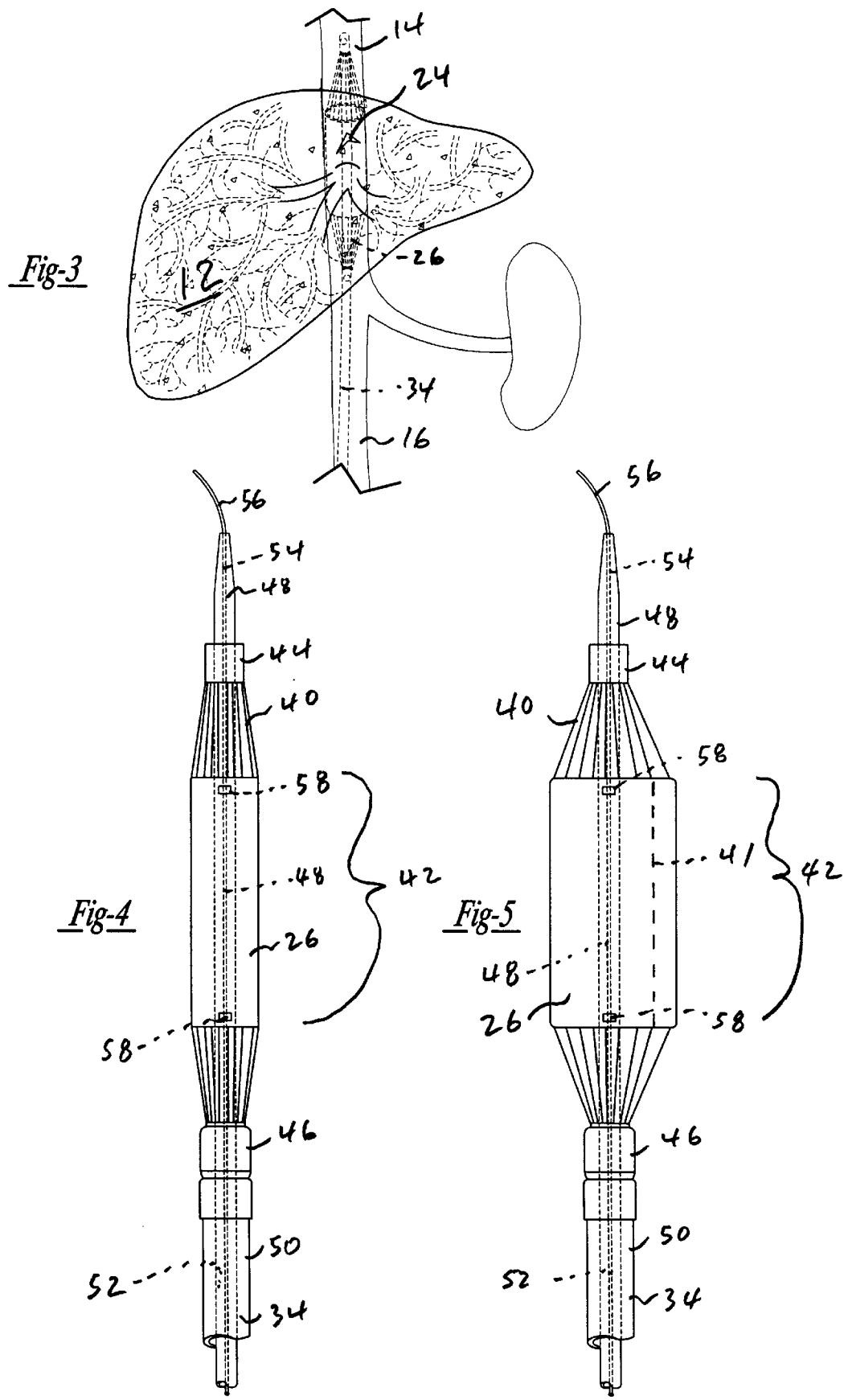

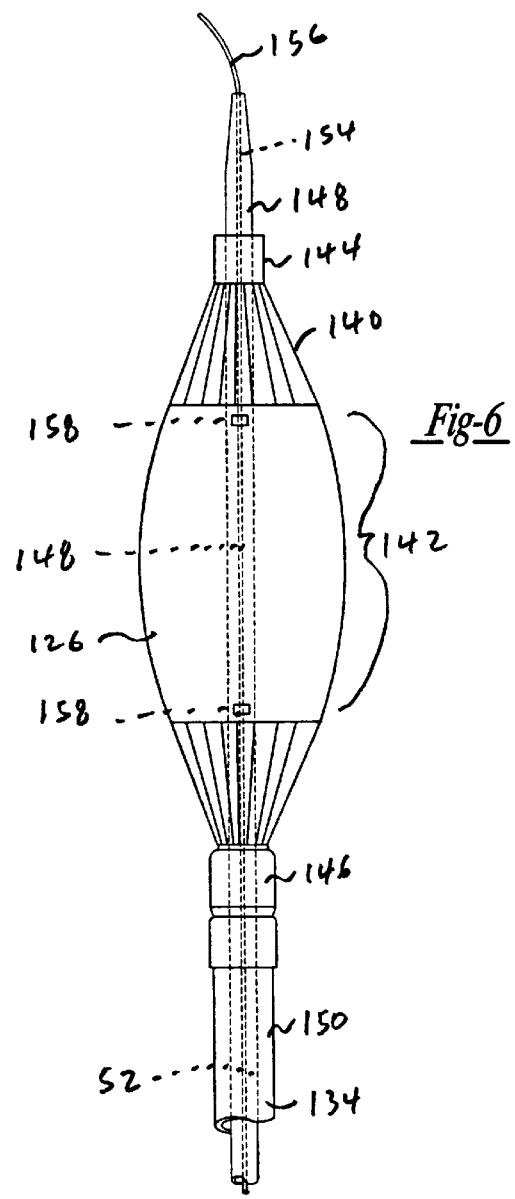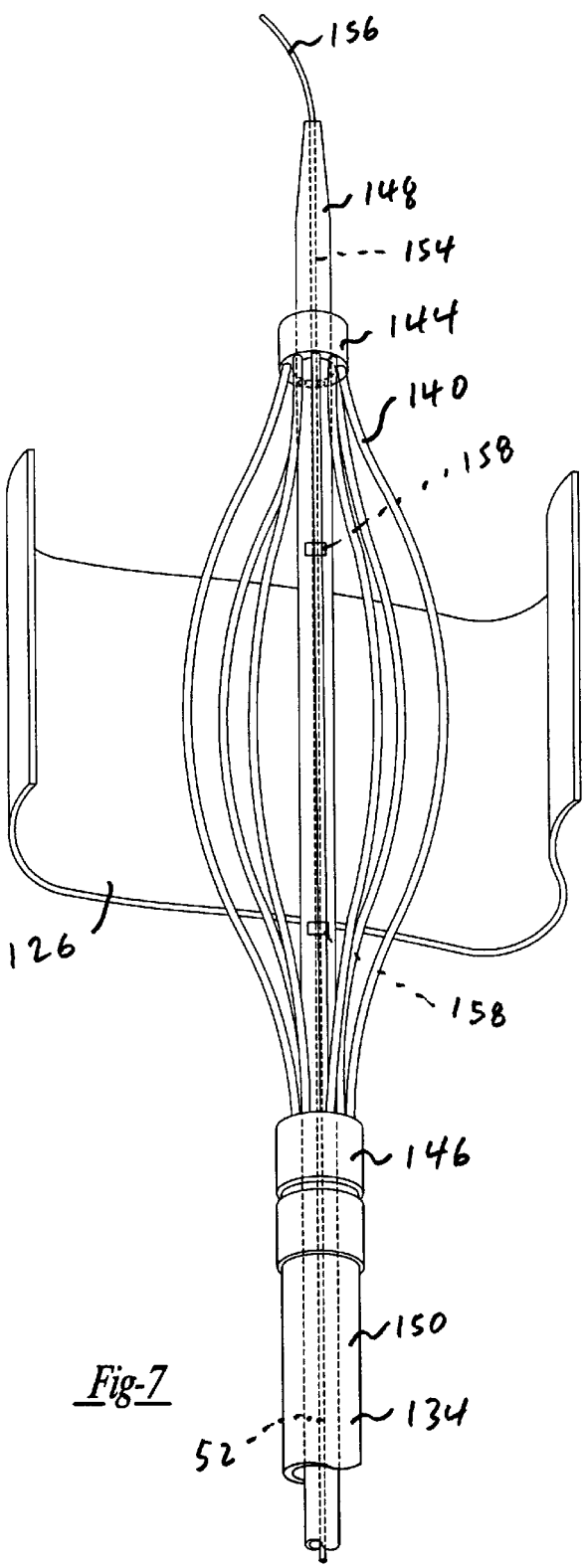

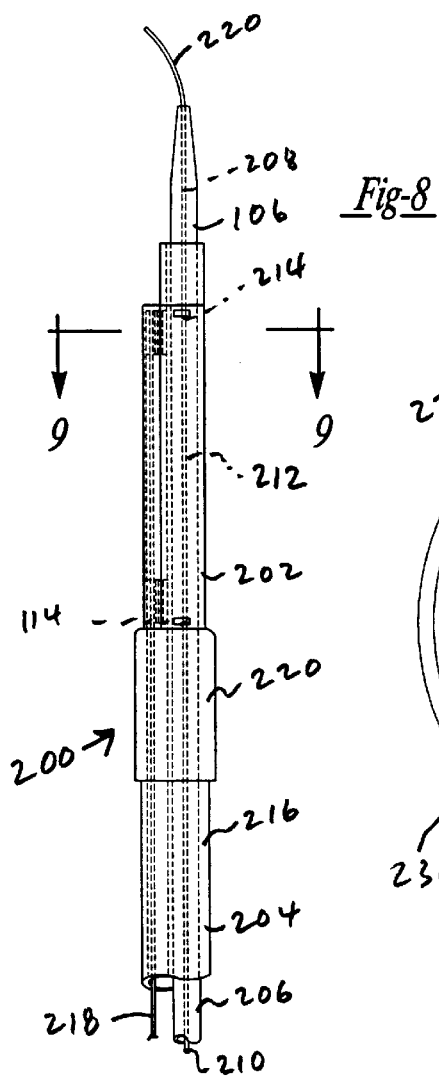
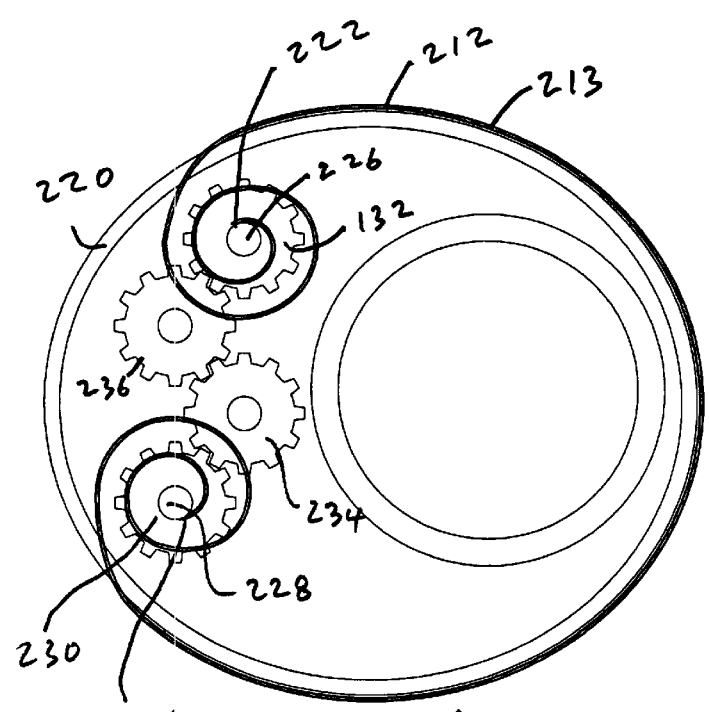
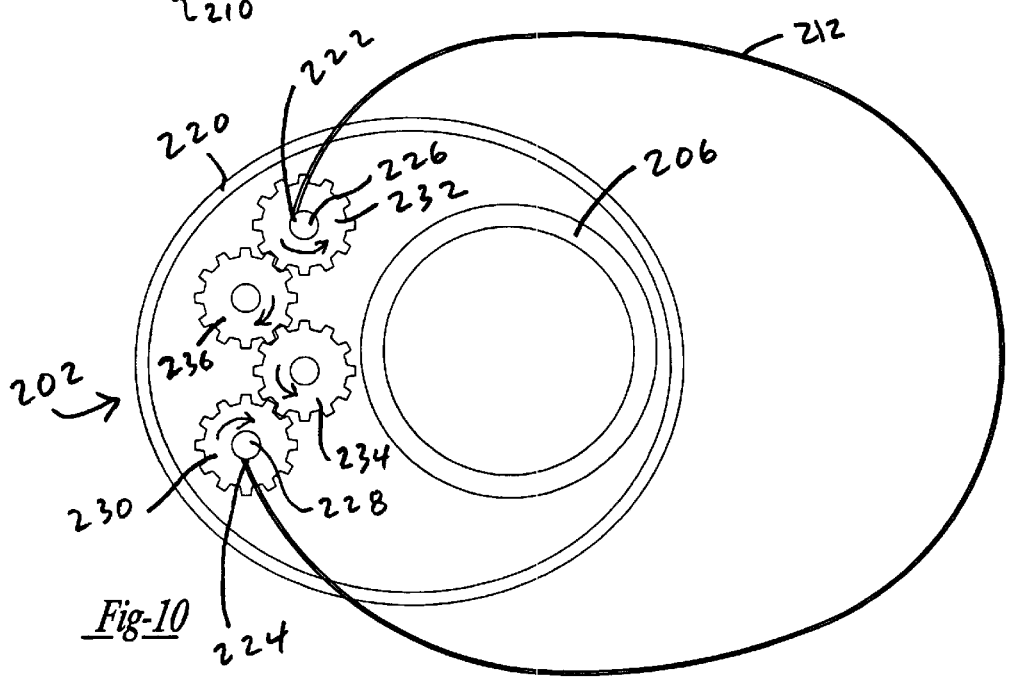

TEMPORARY INTRAVASCULAR STENT FOR USE IN RETROHEPATIC IVC OR HEPATIC VEIN INJURY

BACKGROUND OF THE INVENTION

1. Technical Field

The present invention relates generally to temporary stents for use in providing a temporary halt to blood flow in venal injury. More particularly, the present invention provides a temporary intravascular stent for use in retrohepatic IVC or hepatic vein injury which is capable of expanding to the appropriate size of a blood vessel without reducing preload.

2. Summary of Related Art

Historically, many severely injured persons have not benefitted from the facilities of the hospital emergency room because the severity of their injuries prohibited them from arriving on the surgical table in a timely manner. However, as prehospital care has improved, more severely injured patients have appeared in emergency rooms of hospitals within an appropriate time of the injury. Nevertheless, even in the improved environment of today's prehospital care, the nature of many injuries challenges even the best skills. For example, while injuries to the vessels lying behind the liver account for only about ten percent of overall liver trauma, such injury carries a grave prognosis. Only between fifty and fifty-five percent of these patients arrive at the hospital alive. Even out of this relatively small number, these patients demonstrate an astonishing mortality rate of between seventy and ninety-five percent. Sadly, little advancement has been made over the past twenty ears in the treatment of this type of injury which knows no age group and afflicts both children and adults.

An array of medical deices designed to address this type of problem have been developed. Such devices include the atriocaval shunt and the saphenofemoral balloon shut. In addition, different methods have been attempted in the resolution of such injury. Such methods include the venovenous bypass, total vascular occlusion of the liver, and transection of the supra hepatic vena cava.

The saphenofemoral balloon shunt provides several advantages to the other devices and methods in that it avoids an emergent thoracotomy while offering simplicity in its insertion. This type of device does, however, have some significant disadvantages. Specifically, the saphenofemoral balloon shut significantly decreases blood return to the heart, exact position of the balloon cannot be determined and the balloon may migrate causing vascular compromise to other organs. In addition, the exact position of the balloon cannot be determined at any given time.

The inventor of the present invention recognized that one possible solution to the above-described injury is the intravascular stent. A survey of known stents, however, reveals that there are no known stents which would lend themselves toward the effective resolution of the problem.

U.S. Pat. No. 5,151,105, issued Sep. 29, 1992 to Kwan-Gett, discloses an implantable collapsible tubular sleeve for use in a fluid vessel. The stent includes an inner body portion having an inner coiled wire spring. At each end of the stent is provided a pair of circular support members.

U.S. Pat. No. 5,282,824, issued on Feb. 1, 1994, to Gianturco, discloses a self-expanding stent assembly for use within a body passageway. The assembly includes a plurality of Z-shaped stents which are arranged to form an internal cage. An external nylon sleeve is fitted over the cage.

U.S. Pat. No. 5,344,444, issued Sep. 6, 1994, to Glastra, discloses an expandable cylinder formed from a hollow expandable ring or sleeve which may be inserted into a body vessel. With specific reference to FIG. 11, an expandable tube 40 includes an outer wall 42, an inner wall 44, and end walls 46 and 48.

U.S. Pat. No. 5,356,423, issued Oct. 18, 1994, to Tihon et al. discloses a resectable self-expanding stent having a fenestrated side wall. The stent includes a generally tubular member having a pair of opposed ends and a fenestrated wall surface.

U.S. Pat. No. 5,411,549, issued May 2, 1995, to Peters discloses a selectively expandable and retractable stent which may be rolled and unrolled. With particular reference to FIG. 5, the stent 10 includes a tubular section 12 (shown in FIGS. 1 through 3) and a rectangular body portion which is capable of being wrapped onto itself prior to insertion into the vessel.

U.S. Pat. No. 5,474,563, issued Dec. 12, 1995, to Myler et al. discloses a cardiovascular stent and a tool for its retrieval. The stent comprises a generally tubular body having a central lumen which extends between its proximal end and its distal end. An outer sheath is provided.

U.S. Pat. No. 5,634,941, issued Jun. 3, 1997, to Winston et al. discloses a graft bypass apparatus which is movable between a collapsed state for insertion to an expanded state in its operating position. The apparatus or stent is in the form of a thin sheet which is initially flat but which may be wound up tightly around a spool into a roll. The stent naturally tends to expand. An expandable tubular graft is fitted around the stents. The graft includes a plurality of pleats or folds.

U.S. Pat. No. 5,690,643, issued Nov. 25, 1997, to Wijay discloses a stent delivery system which comprises a movable inner tube and a fixed outer tube. The stent is of the expandable type and is expanded by movement of the inner tube which is axially manipulated with respect to the outer tube so that the undulations or bends effect expansion of the stent.

U.S. Pat. No. 5,730,698, issued Mar. 24, 1998, to Fischell et al. discloses a balloon expandable temporary radioisotope stent system. The system includes an angioplasty catheter and a stent. As illustrated best between FIGS. 1 and 5, a stent 31 is provided on a balloon angioplasty catheter 20. The distal end of the stent 31 is fixed to the distal section of the catheter 20 and the proximal end of the temporary stent 31 is fixed to a distal end of a pusher tube 32. The pusher tube 32 cooperates with the proximal section of the balloon angioplasty catheter 20 and allows the stent 31 to be reversibly deployed in a radially outward manner.

U.S. Pat. No. 5,735,869, issued Apr. 7, 1998, to Fernandez-Aceytuno discloses a balloon catheter and stent delivery device. The balloon catheter is intended for carrying a balloon expandable stent into a body vessel. The catheter includes a dilation balloon.

U.S. Pat. No. 5,800,522, issued Sep. 1, 1998, to Campbell et al. discloses a tube for insertion into a blood conduit and the like. The tube in the form of a liner is secured by the stent.

While representing developments in the art, known stents fail to provide a satisfactory temporary vascular stent having particular application in retrohepatic IVC or hepatic vein injury. Accordingly, advancements in the field remain wanting.

SUMMARY OF THE INVENTION

A peripherally inserted retractable transvenous conduit may be created to temporarily provide hemostasis in injuries to vessels behind the liver without significantly impeding blood return to the heart. Such a device, if correctly configured, will function properly at differing blood flows, pressures, and vessel diameters. Position of such a conduit can be confirmed by endovascular ultrasound.

Accordingly, the present invention relates to a temporary stent for use in retrohepatic IVC or hepatic vein injury which is capable of expanding to the appropriate size of a blood vessel without reducing preload. In general, a collapsible stent is provided which may expand to the appropriate size of the vessel without reducing preload.

In a first embodiment, the stent includes an outer sheath made of a very thin, expandable and impermeable material such as Gortex [trademark]. An internal skeleton is comprised of a plurality of axial support members. One end the axial support members terminate collectively on an inner guide wire. The other end the axial support members terminate collectively on an outer guide wire. Expansion is effected by movement of one guide wire relative to the other such that the collective termination points of the ends of the stent are moved toward one another.

In a second embodiment, a rotatable gear arrangement is provided with two shafts for selectively playing out and reeling in an expandable sheath. According to this embodiment, the stent sheath is movable between a rolled position and an unrolled position and is unrolled once delivered to the desired site.

Optionally, and regardless of the embodiment, the stent of the present invention may be fitted with probes so that the stent might demonstrate ultrasonic assessment capabilities to allow exacting implantation. An external sensor is connected to a video monitor. Upon insertion, the attending physician can track the placement of the stent within the vein to a very high degree of accuracy by relying upon the capabilities provided through the ultrasound system. In addition to tracking, the ultrasonic capabilities optionally provided in conjunction with the stent allow the attending physician to control the expansion of the stent to a size appropriate for the vessel involved.

The present invention provides a new method in the treatment of injuries to vessels behind the liver. It also should improve the survival rates of such a serious injury. Furthermore, the conduit of the present invention may find applications beyond hepatic injury. For example, the conduit of the present invention may be adapted to be used in other instances such as ruptured abdominal aortic aneurysms which also demonstrate mortality rates of about fifty percent. In fact, the present invention has application to all ruptures of arteries and veins which are difficult to expose and control prior to repair. For example, the present invention may be particularly useful in providing temporary hepatic vein occlusion during resection surgery to markedly reduce blood loss.

BRIEF DESCRIPTION OF THE DRAWINGS

The present invention will be more fully understood by reference to the following detailed description of the preferred embodiments of the present invention when read in conjunction with the accompanying drawings, in which like reference characters refer to like parts throughout the views, and in which:

FIG. 3 is diagrammatic view similar to that of FIG. 2 but showing the stent of the present invention in its expanded configuration at the approximate site of the injury;

FIG. 4 is a plan view of the preferred embodiment of the stent of the present invention in its insertion (folded) configuration and a partial plan view of the insertion and manipulating cable assembly;

FIG. 5 is a view similar to that of FIG. 4 but illustrating the stent in its expanded configuration;

FIG. 6 is a plan view of a variation of the preferred embodiment shown in FIGS. 4 and 5 illustrated in its expanded configuration;

FIG. 7 is a view similar to that of FIG. 6 but showing greater detail of the stent;

FIG. 8 is a plan view of an alternate embodiment of the stent of the present invention in its insertion (folded) configuration and a partial plan view of the insertion and manipulating cable assembly;

FIG. 9 is sectional view of the alternate embodiment of the stent of the present invention taken along line 9—9 of FIG. 8 and illustrating the stent in its insertion (folded) configuration;

FIG. 10 is a view similar to that of FIG. 9 but showing the stent in its expanded configuration.

DETAILED DESCRIPTION OF THE PREFERRED EMBODIMENT

The drawings disclose the preferred embodiment of the present invention. While the configurations according to the illustrated embodiment are preferred, it is envisioned that alternate configurations of the present invention may be adopted without deviating from the invention as portrayed. The preferred embodiment is discussed hereafter.

Figure 1:
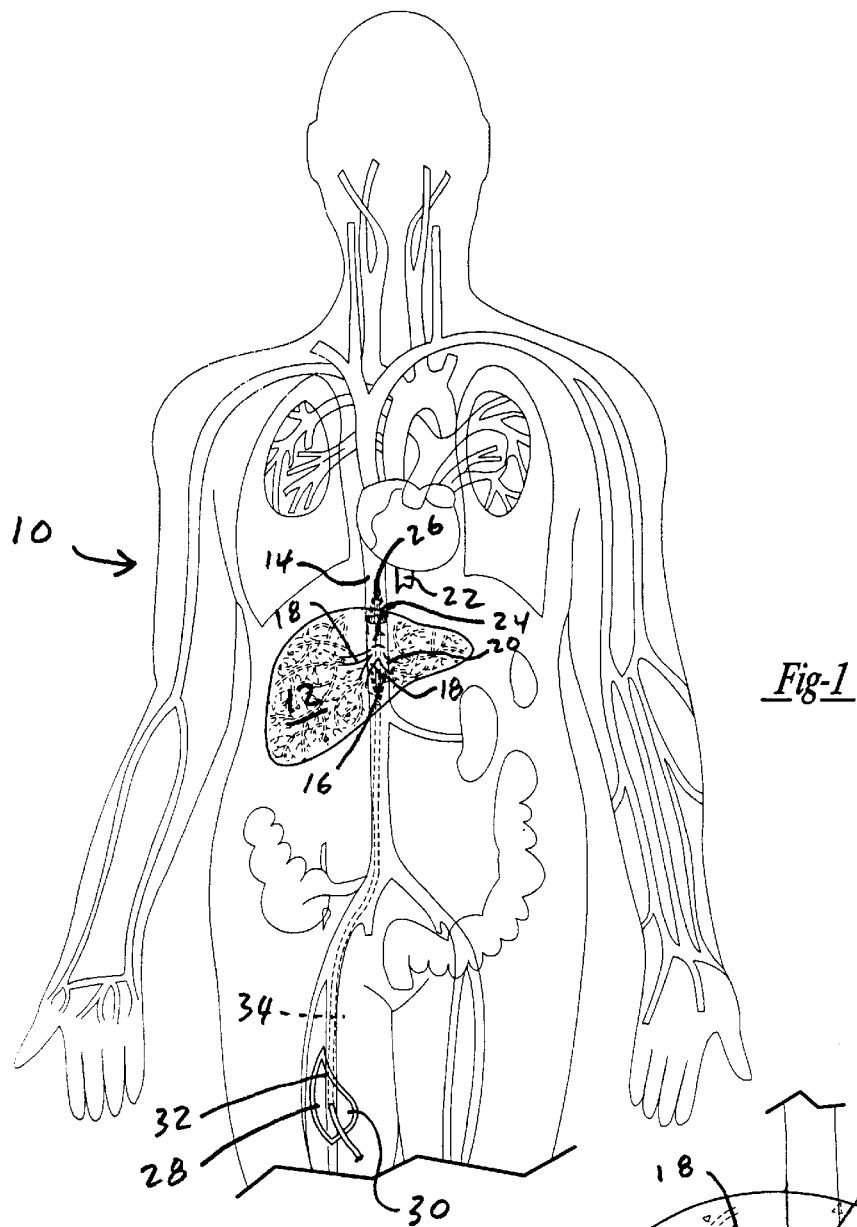
FIG. 1 is a diagrammatic view of the main vessels and certain ones of related organs of the human body showing a stent in place following insertion.

FIG. 1 illustrates a diagrammatic view of the main vessels and certain ones of related organs of the human body, generally illustrated as 10. Of interest for purposes of the present disclosure are the liver 12, the suprahepatic vena cava 14, the infrahepatic vena cava 16, the right hepatic vein 18, the left hepatic vein 20, and the aorta 22.

A classic injury at the approximate confluence of the right hepatic vein 18 and the left hepatic vein 20 is illustrated as 24. While the injury 24 is well-known, other injuries can as well occur at different locations along the vena cava which may as well be effectively treated by the stent of the present invention. Accordingly, the illustrated injury 24 should be interpreted as exemplary of the applications of the present invention and not limiting.

A stent 26 is shown in position to block blood flow and to allow surgical repair of the damaged tissue. In the illustration, a point of insertion 28 has been formed through the right thigh 30 and into the right femoral vein 32. A manipulating cable assembly 34 is shown in shadow lines. The stent 26 is fitted to the distal end of the cable assembly 34.

Figure 2:
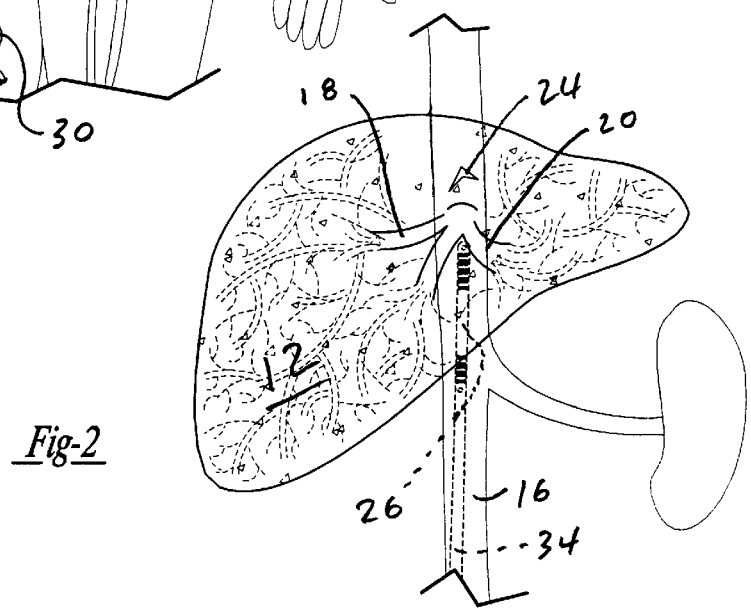
FIG. 2 is a diagrammatic view of a classic, high blood loss injury to the vena cava at the location defining the approximate confluence of the right hepatic vein and the left hepatic vein and illustrating the stent according to the present invention in its insertion (folded) configuration being directed to the site of the injury.

FIG. 2 is a diagrammatic view of the classic, high blood loss injury 24 generally shown in FIG. 1. The dramatic effusion of blood effected by the injury 24 is illustrated. The stent 26 (illustrated in shadow lines) as illustrated is being positioned toward the site of the injury 24 through manipulation by the attending physician (not shown) of the cable assembly 34 (also not shown). The stent 26 is shown in its insertion (folded) configuration.

FIG. 3 is a diagrammatic view similar to that of FIG. 2 but showing the stent 26 in its expanded configuration adjacent the hepatic injury. In this position, the blood flow has been halted or minimized such that suturing of the injury site can be undertaken. Once reparation of the injury has been effected, the stent 26 is allowed to relax to its insertion (folded) configuration. The stent 26 is withdrawn by manipulation of the cable assembly 34 in the direction opposite insertion.

FIGS. 4 and 5 illustrate the preferred embodiment of the stent 26 in both its insertion (folded) configuration and its expanded configuration. It is the embodiment of the stent 26 which is illustrated in FIGS. 1–3, but the alternate configuration of the stent 26 (shown in FIGS. 6–11 and discussed in conjunction therewith) may be selectively used as well.

With respect to FIG. 4, a plan view of the stent 26 is illustrated in its insertion (folded) configuration. The stent 26 includes an expandable outer sheath 36 which is expanded and positioned to form the barrier to blood loss at the site of the injury. The outer sheath 36 may be made of a variety of elastic, durable polymerized materials such as Gortex (trademark) or may be made of nylon, latex, or any other fluid-impermeable material. While a variety of materials may be used for this purpose, it is important that the material be capable of forming a temporary barrier to the flow of blood.

Underlying the outer sheath 36 is a cage 38. The cage 38 comprises a plurality of parallel elongated ribs 40. While the ribs 40 may be composed of a variety of materials, a shape-memory material is desired. For example, shape memory Nitinol alloy wire may be the material of choice. The relatively low profile of the individual ribs 40 illustrated in FIG. 4 is the ordinary, non-flexed state. While a number of individual ribs 40 are illustrated, this number may be altered so as to be greater or lesser as preferred.

Each of the ribs 40 includes a relatively straight portion 41 (illustrated in shadow lines in FIG. 5). The relatively straight portion 41 may be composed of a relatively inflexible material that is more rigid that the rest of the rib 40 or may be fitted with a reinforcing element such as a reinforcing sleeve (not shown).

The individual ribs 40 of the cage 38 collectively define a central region 42. The sheath 36 is fitted to the central region 42 so as to define a continuous surface having a tubular, open-ended configuration. The sheath 36 may be stretch-fitted or may be fastened to the cage 38.

Each of the ribs 40 is anchored at each of its ends to one or the other of a pair of spaced-apart collars 44, 46. One of these collars, the distal or fixed collar 44, is anchored to a guide shaft 48. The other of the these collars, the proximal or slidable collar 46, is fixed to the distal end of a movable shaft 50. The movable shaft 50 includes an axially formed central aperture 52 through which the guide shaft 48 may be moved.

Through the guide shaft 48 is axially formed a central aperture 54 within which a flexible guide wire 56 is movably disposable.

Optionally, one or more ultrasonic elements 58 may be fitted generally to the guide shaft 48 as illustrated. The elements 58 are ultrasound-responsive and provide the stent 26 with ultrasonic capabilities by providing a reflection surface against which ultrasonic radiation may be reflected to a receiving unit. The elements 58 may be composed of a material which is readily sensed by ultrasonic frequencies, such as a metal or a rigid polymerized plate. The position of the stent 26 may thereafter be monitored during insertion and removal to provide accurate positioning by the site of the injury.

In operation, the attending surgeon extends the guide wire 56 from the illustrated tapered tip at the distal end of the guide shaft 48. The distal end of the guide wire 56 is then inserted into the entrance formed in the femoral artery. The surgeon manipulates the guide wire 56 through the appropriate vessels until it is in its approximate position adjacent the site of the injury as determined by the length of the wire 56. The stent 26 is next inserted through the femoral artery opening by the surgeon pushing against the guide shaft 48. The guide shaft 48 follows the previously inserted guide wire 56.

If fitted with the optional ultrasonic elements 58, an ultrasonic sensor is used to follow the progress of the stent 26 until it reaches the location of the injury. Otherwise, the surgeon relies upon the length of the shaft 48 to determine correct placement.

Once in its desired position, the surgeon holds the guide shaft 48 with one hand and with the other hand slides the movable shaft 50 forward a few millimeters. This movement forces the ribs 40 to expand radially from their unflexed, relaxed positions illustrated in FIG. 4 to the stressed, expanded positions illustrated in FIG. 5. When in the configuration illustrated in FIG. 5, the sheath 36 is expanded radially outwardly to its blood-flow blocking position. The attending surgeon then locks the movable shaft 50 against axial movement with respect to the guide shaft 48 by a locking device (not shown). Surgical repair of the damaged tissue may thus be made.

FIGS. 6 and 7 illustrate a variation of the first preferred embodiment of the present invention. FIG. 6 illustrates a view of a stent, generally illustrated as 126, in its expanded state. The stent 126 includes an expandable outer sheath 136 which, as with the sheath 36 of the stent 26 described above, is expanded and positioned to form the barrier to blood loss at the site of the injury. FIG. 7 illustrates a more detailed view of the stent 126 with the sheath 136 having been pulled partially away for illustrative purposes.

Underlying the outer sheath 136 is a cage 138. The cage 138 comprises a plurality of elongated ribs 140. Noteworthy is the shape difference of the ribs 140 as compared to the ribs 40 set forth in FIGS. 4 and 5. The curvilinear shape of the ribs 140 allows for the crest area of the outwardly expanded sheath 136 to be applied more directly to the injury site as may be needed.

The individual ribs 140 of the cage 138 collectively define a central region 142. The sheath 136 is fitted to the central region 142 so as to define a continuous surface having a tubular, open-ended configuration.

Each of the ribs 140 is anchored at each of its ends to one or the other of a pair of spaced-apart collars 144, 146. One of these collars, the distal or fixed collar 144, is anchored to a guide shaft 148. The other of the these collars, the proximal or slidable collar 146, is fixed to the distal end of a movable shaft 150. The movable shaft 150 includes an axially formed central aperture 152 through which the guide shaft 148 may be moved.

Through the guide shaft 148 is axially formed a central aperture 154 within which a flexible guide wire 156 is movably disposable.

Optionally, and as with the embodiment illustrated and discussed above with respect to FIGS. 4 and 5, one or more ultrasonic elements 158 may be fitted generally to the guide shaft 148 as illustrated. The elements 158 provide the stent 126 with ultrasonic capabilities by providing a reflection surface against which ultrasonic radiation may be reflected to a receiving unit. The position of the stent 126 may thereafter be monitored during insertion and removal to provide accurate positioning by the site of the injury.

Use of the stent 126 is substantially the same as described above with respect to the stent 26.

FIGS. 8 through 11 illustrate an alternate embodiment of the present invention. This variation discloses a stent assembly, generally illustrated as 200. The assembly 200 includes a stent portion 202 and a manipulating cable assembly 204. The stent portion 202 is fixed to the distal end of the cable assembly 204.

With specific reference to FIG. 8, a plan view of the stent assembly 200 is illustrated in its insertion (folded) configuration. As can be seen, the assembly 200 shares some features in common with the stent 26 discussed above and illustrated in FIGS. 1 through 5. The stent portion 202 includes a guide shaft 206 having an axially formed central aperture 208 within which a flexible guide wire 210 is movably disposed. The guide wire 210 and its operation is the same as that set forth above with respect to the stent 26.

Figure 11:
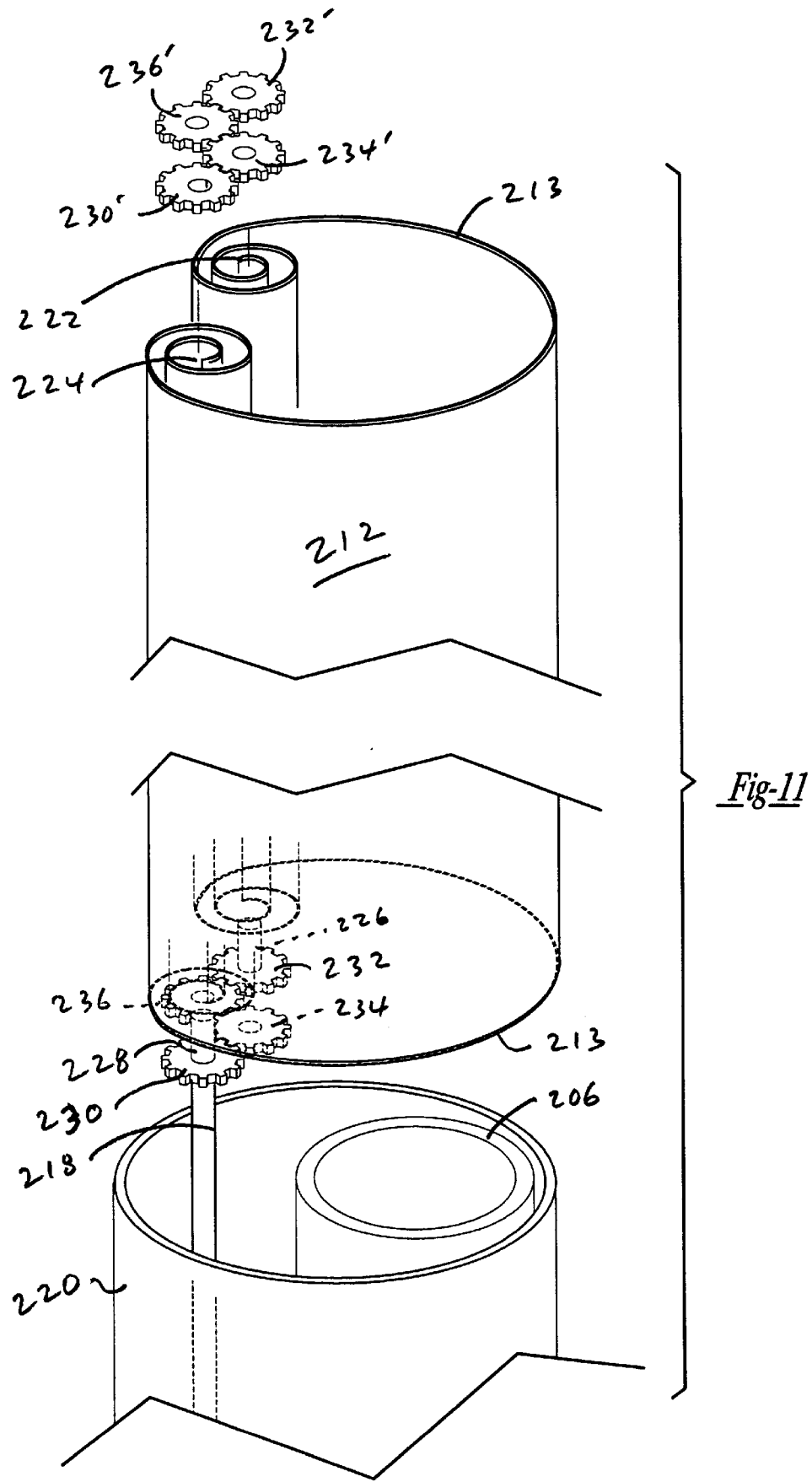
FIG. 11 is an exploded perspective view illustrating the arrangement of the driving, driven, and idle gears as well as the flexible component in relation to the manipulating cable assembly.

The stent portion 202 additionally includes an expandable sheath 212. The sheath 212 is preferably composed of a fluid-resistant polymerized material. The sheath 212 may include a resilient reinforcing ring 213 at each of its ends. The pair of rings 213 is best shown in FIG. 11.

Optionally, a plurality of ultrasonic elements 214 may be fitted generally to the guide shaft 206. The elements 214 provide the same function as the elements 58 discussed above with respect to the stent 26 and discussed in relation to FIGS. 4 and 5.

The manipulating cable assembly 204 includes a substantially hollow outer sleeve 216 which encases a portion of the guide shaft 206 (within which is provided the guide wire 210 as illustrated) and a rotatable drive wire 218. A collar 220 joins the stent portion 202 and the cable assembly 204.

FIG. 9 is a sectional view of the stent assembly 200 taken along line 9—9 of FIG. 8. This view illustrates the stent assembly 200 in its insertion (folded) configuration. The sheath 212 includes a first end 222 and a second end 224. The first end 222 is connected to a first drive shaft 226 and the second end 224 is connected to a second drive shaft 228. The second drive shaft 228 is connected to a proximal drive gear 230. The first drive shaft 226 is connected to a proximal driven gear 232. The proximal drive gear 230 has a distal side (to which the second drive shaft 228 is connected) and a proximal side. (The distal end of the rotatable drive wire 218 is fixed to the proximal side of the drive gear 230 as illustrated in FIG. 11, to be discussed below.)

The proximal drive gear 230 is operatively meshed with a first proximal idler gear 234 which is, in turn, operatively meshed with a second proximal idler gear 236. The second proximal idler gear 236 is operatively meshed with the proximal driven gear 232.

In operation, and with respect to both FIGS. 9 and 10, when the proximal drive gear 230 is rotated, rotation of the proximal driven gear 232 is effected in a direction opposite that of the drive gear 230 through translation of movement via the first proximal idler gear 234 and the second proximal idler gear 136. If the proximal drive gear 230 is caused to be rotated in a first direction, the ends of the sheath 212 are caused to be taken up on the shafts 226 and 228 such that the sheath 212 is folded into its insertion configuration, as illustrated in FIG. 9. If the proximal drive gear 230 is caused to be rotated in a second direction opposite that of the first direction, the ends of the sheath 212 are caused to be let out from the shafts 226 and 228 so that the sheath 212 is extended to its operational position, as illustrated in FIG. 10.

FIG. 11 is an exploded perspective view of the assembly 200 illustrating the arrangement of the driving, driven, and idle gears of the stent portion 202 as well as partially illustrating the cable assembly 204. This view illustrates the spatial arrangement of the proximal drive gear 230, the first proximal idler gear 234, the second proximal idler gear 236, and the proximal driven gear 232. This view also illustrates the distal arrangement of drive and driven gears and includes a distal drive gear 230' which is mated to the proximal drive gear 230 via the drive shaft 228, a first distal idler gear 234', a second distal idler gear 236', and a distal driven gear 232' which is mated to the proximal driven gear 232 via the drive shaft 226. The arrangement of the proximal gears 230, 234, 236, and 232 and the distal gears 230', 234', 236', and 232' effects simultaneous rotational operation in like directions via the shafts 226 and 228.

As noted above, the rotatable drive wire 218 is fixed to the proximal side of the drive gear 230. Selective rotation of the drive wire 218 in a first or second direction effects rotation of all of the gears and thus causes extension or retraction of the sheath 212.

In operation, the attending surgeon extends the guide wire 210 from the illustrated tapered tip at the distal end of the guide shaft 206. The distal end of the guide wire 210 is then inserted into the entrance formed in the femoral artery. The surgeon manipulates the guide wire 210 through the appropriate vessels until it is in its approximate position adjacent the site of the injury as determined by the length of the wire 210. The stent assembly 200 is next inserted through the femoral artery opening by the surgeon pushing against the manipulating cable assembly 204. The guide shaft 206 follows the previously inserted guide wire 210.

If fitted with the optional ultrasonic elements 214, an ultrasonic sensor is used to follow the progress of the stent portion 202 until it reaches the location of the injury. Otherwise, the surgeon relies upon the length of the cable assembly 204 to determine correct placement.

Once in its desired position, the surgeon holds the hollow outer sleeve 216 with one hand and with the other hand rotates the rotatable drive wire 218 in a direction such that the sheath 212 is caused to be let out. The rotation of the drive wire 218 is continued until the outer side of a portion of the sheath 212 is pressed against the injury site thus blocking the flow of blood. The drive wire 218 is subsequently locked against rotation by a locking device (not shown) and repair of the injury tissue may thus be made.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

What is claimed is:

1. A removable and temporary intravascular stent for use in hepatic vessel injury, the stent comprising:
   a guide shaft;
   a fixed collar fixed to said guide shaft, said fixed collar having a plurality of rib-receiving apertures formed therein;

a movable shaft slidably positioned over a portion of said guide shaft;

a movable collar fixed to said movable shaft, said movable collar having a plurality of rib-receiving apertures formed therein;

an elastic sheath that is substantially impermeable to liquid, said sheath having a tubular configuration; and a skeletal cage composed of a plurality of individual ribs anchored within said rib-receiving apertures formed in said fixed collar and said movable collar, said ribs having a defined first configuration and being composed of a shape-memory material for substantially maintaining said defined first configuration, said ribs being sufficiently flexible to be flexed to a second configuration, said cage having a mid-portion, said elastic sheath being wrapped about said mid-portion, said cage having a first end fixed to said fixed collar and a second end fixed to said movable collar.

2. The removable and temporary intravascular stent of claim 1, further including an aperture axially defined through said guide shaft.

3. The removable and temporary intravascular stent of claim 2, further including a guide wire fitted within said aperture of said guide shaft.

4. The removable and temporary intravascular stent of claim 1, wherein said sheath is open ended.

5. The removable and temporary intravascular stent of claim 1, further including at least one ultrasound-responsive element fitted to said guide shaft.

6. The removable and temporary intravascular stent of claim 5, wherein said ultrasound-responsive element is composed of a metal.

7. The removable and temporary intravascular stent of claim 5, wherein said ultrasound-responsive element is composed of a polymerized material.

8. The removable and temporary intravascular stent of claim 1, wherein each of said ribs has a configuration, said configuration being substantially straight.

9. The removable and temporary intravascular stent of claim 1, wherein each of said ribs has a configuration, said configuration including a first end part, a middle part, and a second end part, said parts each being substantially straight.

10. The removable and temporary intravascular stent of claim 9, wherein said first end part is connected to and angled with respect to said middle part and said second end part is connected to and angled with respect to said middle part.

11. A removable and temporary intravascular stent for use in hepatic vessel injury, the stent comprising:

a guide shaft;

a fixed collar fixed to said guide shaft, said fixed collar having a plurality of rib-receiving apertures formed therein;

a movable shaft slidably positioned over a portion of said guide shaft;

a movable collar fixed to said movable shaft, said movable collar having a plurality of rib-receiving apertures formed therein, said movable collar being movable between a first unflexed, insertion-removal position and a second, flexed, fluid-blocking position;

an elastic sheath that is substantially impermeable to liquid, said sheath having a tubular configuration; and a skeletal cage composed of a plurality of individual ribs anchored within said rib-receiving apertures formed in said fixed collar and said movable collar, said ribs each having a substantially straight configuration and being composed of a material that is flexible enough to allow said ribs to be flexed to a generally outwardly bowed state with respect to said guide shaft when said movable collar is moved to said second position.

12. The removable and temporary intravascular stent of claim 11, further including an aperture axially defined through said guide shaft.

13. The removable and temporary intravascular stent of claim 12, further including a guide wire fitted within said aperture of said guide shaft.

14. The removable and temporary intravascular stent of claim 11, wherein said sheath is open ended.

15. The removable and temporary intravascular stent of claim 11, further including at least one ultrasound-responsive element fitted to said guide shaft.

16. The removable and temporary intravascular stent of claim 15, wherein said ultrasound-responsive element is composed of a material selected from the group consisting of a metal and a polymerized material.

17. A removable and temporary intravascular stent for use in hepatic vessel injury, the stent comprising:

a manipulating cable assembly, said cable assembly including a substantially hollow outer sleeve an a rotatable drive wire;

a stent portion attached to said manipulating cable assembly, said stent portion including a guide shaft having an axially formed central aperture, a flexible guide wire movably disposed within said guide shaft, an expandable sheath having a first end and a second end, said stent portion further including a driving assembly, said driving assembly including a first drive shaft to which said first end of said sheath is connected and a second drive shaft to which said second end of said sheath is connected, said first drive shaft being connected to said rotatable drive wire, said first drive shaft and said second drive shaft being operatively connected such that when said first drive shaft is rotated in one direction by said rotatable drive wire, said second drive shaft is rotated in the opposite direction, thereby selectively folding or unfolding said sheath upon said first and second drive shafts.

18. The removable and temporary intravascular stent of claim 17, wherein said sheath is composed of a fluid-resistant polymerized material.

19. The removable and temporary intravascular stent of claim 17, wherein said sheath includes two ends, each of said two ends being fitted with a resilient reinforcing ring.

20. The removable and temporary intravascular stent of claim 17, wherein said stent portion is fitted with at least one ultrasound-responsive element.

21. The removable and temporary intravascular stent of claim 20, wherein said ultrasound-responsive element is composed of a material selected from the group consisting of a metal and a polymerized material.

* * * * *